United States Patent [19]
Hamann

[11] Patent Number: 6,153,621
[45] Date of Patent: Nov. 28, 2000

[54] COMBINED ANTAGONIST COMPOSITIONS

[75] Inventor: Scott R. Hamann, Nicholasville, Ky.

[73] Assignee: The University of Kentucky Research Foundation, Lexington, Ky.

[21] Appl. No.: 09/102,089

[22] Filed: Jun. 23, 1998

Related U.S. Application Data

[60] Provisional application No. 60/050,557, Jun. 23, 1997.
[51] Int. Cl.$^7$ ............................ A61K 31/44; A61K 31/13
[52] U.S. Cl. ............................................ 514/282; 514/661
[58] Field of Search ...................................... 514/282, 661

[56] References Cited

U.S. PATENT DOCUMENTS

| | | |
|---|---|---|
| 5,472,943 | 12/1995 | Crain et al. . |
| 5,512,578 | 4/1996 | Crain et al. . |
| 5,580,876 | 12/1996 | Crain et al. . |
| 5,585,348 | 12/1996 | Crain et al. . |
| 5,723,103 | 3/1998 | de Paulis et al. ....................... 424/1.85 |

OTHER PUBLICATIONS

Scott R. Hamann et al., "Opioid and Nicotinic Analgesic and Hyperalgesic Loci in the Rat Brain Stem", The Journal of Pharmacology and Experimental Therapeutics, vol. 261, No. 2, 1992, pp. 707–715.

Scott R. Hamann et al., "Analgesic Actions of Dynorphin A(1–13) Antiserum in the Rat Brain Stem", Brain Research Bulletin, vol. 29, 1992, pp. 605–607.

S.R. Hamann et al., Rapid Communication, "Analgesic Actions of Local Anesthetics and Cobalt Chloride in the Rat Brain Stem", Pharmacology Biochemistry and Behavior, vol. 43, 1992, pp. 925–927.

S.R. Hamann et al., Rapid Communication, "Hyperalgesic and Analgesic Actions of Morphine, U50–488, Naltrexone, and (−)–Lobeline in the Rat Brainstem", Pharmacology Biochemistry and Behavior, vol. 47, 1994, pp. 197–201.

Scott R. Hamann et al., Rapid Communication, "Thermally Evoked Tail Avoidance Reflex: Input–Output Relationships and Their Modulation", Brain Research Bulletin, vol. 29, 1992, pp. 507–509.

Shirin Parvini et al., "Pharmacologic Characteristics of a Medullary Hyperalgesic Center", The Journal of Pharmacology and Experimental Therapeutics, vol. 265, No. 1, 1993, pp. 286–292.

*Primary Examiner*—Russell Travers
*Attorney, Agent, or Firm*—McDermott, Will & Emery

[57] ABSTRACT

Novel compositions of a combination of nicotinic, opioid, serotonergic and/or adrenergic antagonists in combination with nicotinic and opioid agonists, anti-depressants, stimulants, non-steroidal anti-inflammatory drugs, and local anesthetics, such combinations being useful in the treatment of excitable system disorders, pain and psychiatric disorders, and methods of use thereof.

8 Claims, 18 Drawing Sheets

Antagonist Modulation of Naltrexone Hyperalgesia
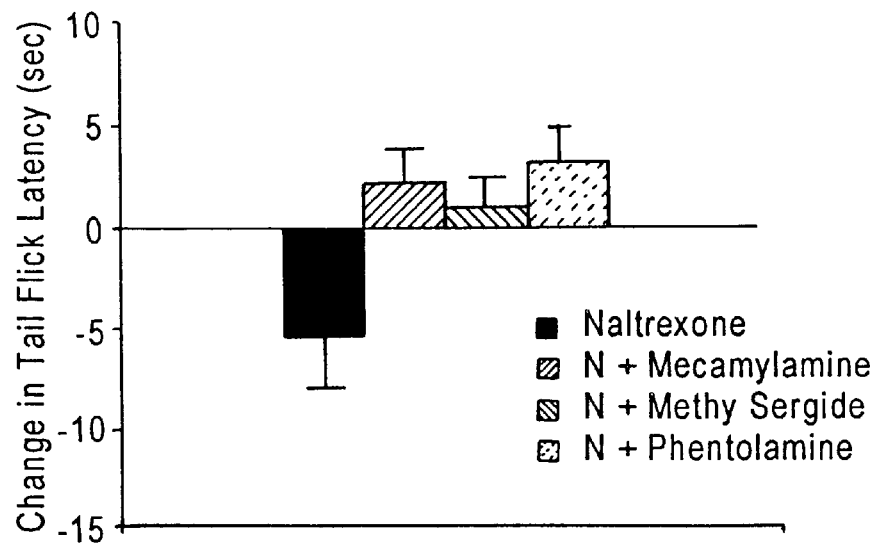
FIG. 11(A-1)
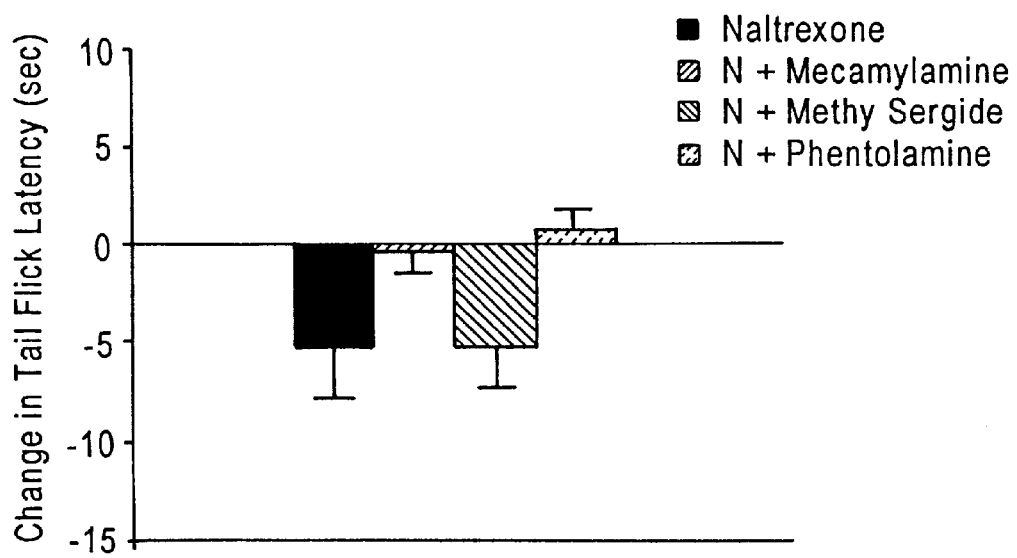
FIG. 11(B-1)

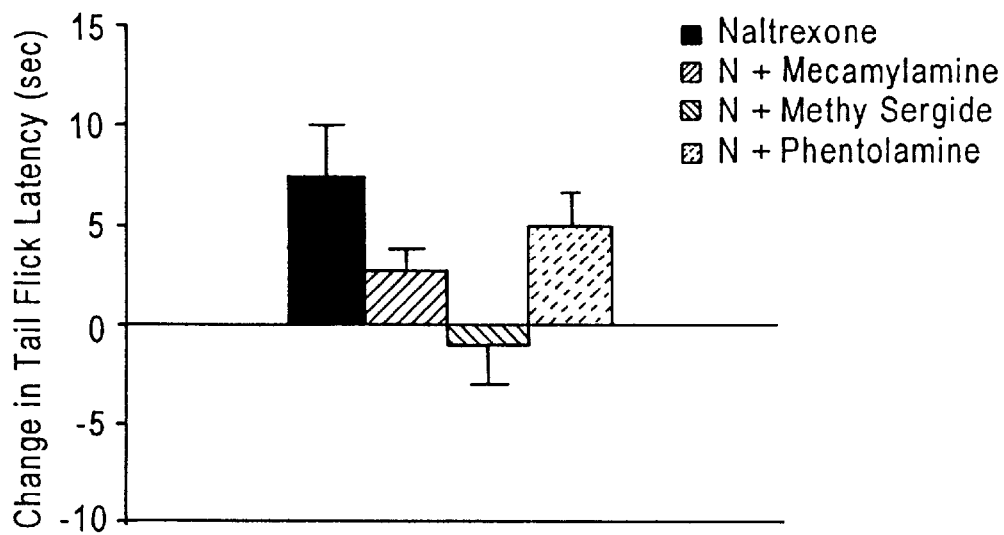
FIG. 11(A-2)
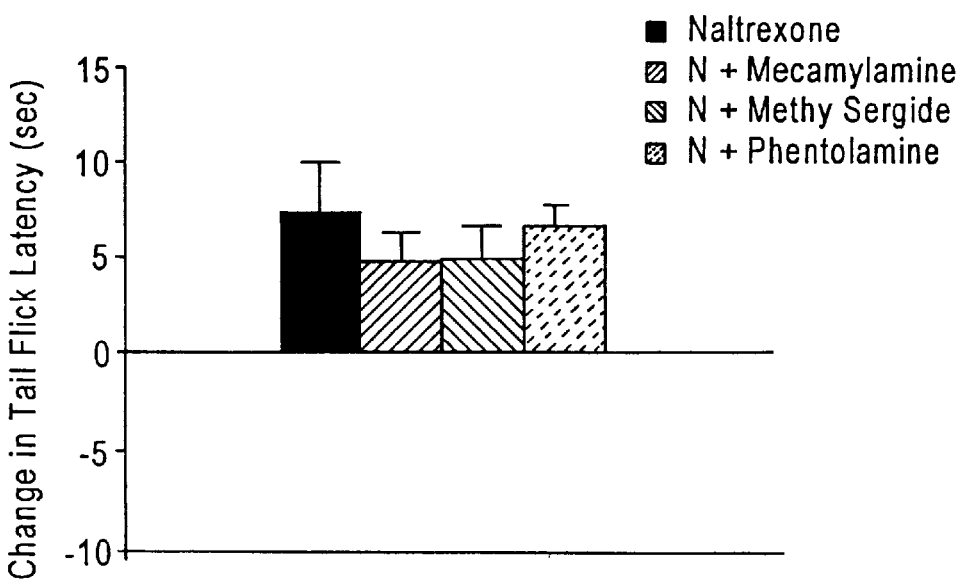
FIG. 11(B-2)

EFFECTS OF NALTREXONE (0.25 MG / KG) + MECAMYLAMINE (0.25 MG / KG)

$$\text{RESPONSE (LITETAR)} = \frac{\text{ANALGESIA (A)}}{\text{HYPERALGESIA (H)}} = \frac{e \cdot Rt \cdot Ag1 / (Ag + Ka)}{e \cdot Rt \cdot Hg1 / (Hg + Kh)}$$

$$\text{Activity} = \frac{\text{Inhibition}}{\text{Excitation}}$$

COMBINED ANTAGONIST COMPOSITIONS

RELATED APPLICATIONS

This application claims priority from U.S. Provisional Patent Application No. 60/050,557 filed Jun. 23, 1997, which is incorporated herein by reference.

TECHNICAL FIELD

The invention relates to pharmaceutical compositions for the treatment of excitable system disorders, including analgesics, anti-excitatory agents, anti-hyperalgesic agents, anti-depressant agents, anti-suffering agents, antisocial personality treatments, conduct disorder treatments, attention deficit treatments and drug abuse treatments. The invention further relates to novel drug combinations of antagonists of excitable system cellular receptor systems and their methods of use in treating excitable system abnormalities, pain and psychiatric disorders. More particularly, the invention relates to compositions which are combinations of nicotinic, opioid, serotonergic and adrenergic antagonists and uses thereof in the treatment of excitable system abnormalities. Exemplary of the compositions of the invention is a combination of a therapeutically effective amount of the nicotinic antagonist mecamylamine and the opioid antagonist naltrexone.

BACKGROUND ART

There exists clinical and scientific evidence for excitatory and inhibitory processes which contribute to excitable system activity, pain and psychiatric disorders. The pharmacologic actions of analgesic and anti-depressant agents prescribed to counteract these disorders are thought to be elicited through interactions with endogenous receptors which alter the activity of excitable systems.

Excitable System Disorders

Clinical depression is characterized by symptoms which include failure to obtain pleasure from activities which previously brought enjoyment. Similarly, individuals experiencing difficulties with alcohol, tobacco, stimulants such as cocaine and narcotic analgesics such as heroin, have a depressive syndrome characterized by one or more of a poor self image, feelings of incompetence and/or inadequacies, alienation, unpopularity and the like. The pathologic feelings of these depressed and/or drug dependent individuals have been collectively called "hypophoria," and are manifest by a general loss of pleasure and interest in most typical activities. Such hypophoric feelings are an essential feature of the persistent depressive state as described by the American Psychiatric Association.

These same hypophoric feelings are also present in many adolescents and are particularly strong in those that have been diagnosed as having conduct disorders. Moreover, it is well established that adolescence and early adulthood is a turbulent time in development when drug abuse, mood and behavior problems emerge. Thus, the lack of coping skills needed to cope with emerging needs in a socially acceptable manner and the ability of psychoactive drugs to decrease the associated discomfort have long been considered related.

Most drugs of abuse, at least on a temporary basis, reverse depressive or hypophoric feelings—an attribute that is, at least in part, thought to be responsible for their reinforcing effects. For heroin, morphine and related drugs, barbiturates, amphetamine, cocaine and marijuana, this role for the anti-hypophoric effect has been unequivocally demonstrated.

When individuals use opioid drugs such as heroin, morphine and the like, they soon become dependent and, upon withdrawal, an abstinence syndrome emerges. Typically, such a syndrome is initially quite discomforting and in many ways resembles a severe flu-like illness, including chills, fever, heightened autonomic tone, and decreased caloric intake. This is followed by a chronic illness characterized by exaggerated responsiveness to stressful and painful stimuli and lessened tone of the autonomic nervous system. This latter phase has been called protracted or secondary abstinence.

Associated with this increased responsiveness to pain are exaggerated feelings of tiredness, lack of energy and social withdrawal, as well as hypophoria. These symptoms are also common to many mood and behavior disorders. Thus, a cycle traps drug abusers and those individuals with mood and behavior disorders in a deepening condition of discontent and hypophoria with a state of continuing vulnerability.

Several studies concerned with the psychiatric profiles of cocaine users have indicated that these patients may exhibit a range of other psychiatric disorders including depression, bipolar disorder, cyclothymia and attention deficit disorders. Further, a variety of drugs of abuse, including morphine-like drugs, amphetamines and barbiturates, produce dose related increases on the Morphine-Benzedrine Group (MBG) scale which measures feelings of well being and contains items which are polarly opposite to the items comprising the hypophoria scale of the Addiction Research Center Maturation Scale (ARCMS). Cocaine's subjective effects are very similar to the effects of amphetamines.

These findings support the hypothesis that many substance abusers have a depressive diathesis and that drugs of abuse provide at least temporary relief from these pre-existing psychopathologies. However, drugs of abuse may worsen pre-existing psychopathologies and therefore further predispose individuals to diseases of pharmacologic adaptation and addiction.

Although the efficacies of currently available anti-depressant preparations are established, a number of prominent problems exist with therapeutic use of these agents. For example, biological heterogeneity of even the most carefully diagnosed patients with depressive diatheses is a fundamental problem facing clinicians. Moreover, less than satisfactory efficacy is a problem in a portion of this patient population, and nearly all of the available anti-depressants have deleterious side effects which are attributable to a lack of specificity, and/or cross-reactivity with regard to endogenous central nervous system processes.

There is thus a need in the art for therapies to effectively treat psychopathologies, including, pain, hypophoria, drug abuse, depression, and the like, that are the result of excitable system disorders and abnormalities.

2. Varied and Paradoxical Response to Psychoactive Drugs

There is wide heterogeneity of patients and their responses to psychoactive drugs used to treat pain and psychiatric diatheses. Patients suffering with chronic pain are often predisposed to depressive states which result in disruption of lifestyle and frequently to use and abuse of drugs.

Research in the past has implicated several chemically and functionally different excitable system neurochemical-receptor systems in central analgesic processes which are evocable and relieve certain painful conditions (i.e., nicotinic and muscarinic cholinergic, catecholamine, serotonin, enkephalins, dynorphins, NMDA and nitric oxide).

Available scientific literature concerned with these processes involved with one of the primary results of excitable system activity disorders, "pain," can be summarized as follows: First, there is duality of function (i.e., excitation vs.

inhibition, analgesia and hyperalgesia, etc.) in every system; Second, there is redundancy of location and function for each system; Third, there is within and between systems modulation of function; and Fourth, there appears to be both within and between species variation in the duality and redundancy of function.

Opioid and nicotinic cholinergic excitation processes have been demonstrated in the pontomedullary and mesencephalic reticular systems of dog and rat.

There appears to be tonic activity of these processes since opioid and nicotinic antagonists (e.g., naltrexone and mecamylamine) produce dose related analgesia when injected into active excitatory sites. There is, however, a high degree of individuality in the activity of these processes as well as in response to antagonists of central neurohumors.

Different populations of inhibitory or facilitatory neurons have also been demonstrated in ventral portions of the brain stem which are involved in analgesic responses to a number of narcotic analgesics. Other investigations have identified spinal opioid "anti-analgesic" processes which involve dynorphin. In addition, both excitatory and inhibitory opioid activity in dorsal root ganglion cell cultures that are associated with changes in regulatory G-protein function have been detected. These studies have all demonstrated the excitatory action of classical opioids such as morphine, as well as an anti-excitatory action of opioid antagonists.

Clinical studies, on the other hand, have reported paradoxical effects of opioid agonists and antagonists. For example, naloxone has been reported to produce both analgesia and hyperalgesia in man. Naloxone also has the ability to both suppress and enhance the response to nociceptive stimuli in animals. In addition, nalaxone enhancement of the analgesic action of nitrous oxide has led to the postulation of an existence of both analgesic and hyperalgesic systems (i.e., duality) in the brain.

With respect to morphine and nicotine, high doses of morphine administered intrathecally produce hyperalgesia in both man and animals, and a number of investigators have shown that nicotine produces analgesia after either parenteral or central administration in a variety of species including the cat, mouse, rat, dog and man. Using muscarinic and nicotinic agonists and antagonists, it has further been demonstrated that nicotine produces analgesia through nicotinic and muscarinic cholinergic mechanisms as well as through opioidergic mechanisms. There is, thus, substantial evidence for distinct nicotinic and muscarinic components involved in the production of analgesia.

Taken together these experimental findings document the existence of excitatory and inhibitory opioid and cholinergic process in several excitable systems.

Similar to opioid and cholinergic processes involved with inhibitory and excitatory influences, the role of biogenic amines, in particular serotonin, has been extensively investigated with contradictory findings prevalent throughout the literature. Early studies using the electrical stimulation and the rat tail flick method showed no effect of methysergide on the thresholds for spinal reflex or vocalization during stimulation, but increases in vocalization after the period of stimulation. There have also been a number of studies showing no effect of systemic methysergide on the tail flick, hot plate and formalin nociceptive assays.

Similarly, hyperalgesia, analgesia or no effect have been reported following systemic administration of metergoline.

As yet other examples, increased sensitivity to nociceptive stimuli has been shown for mianserin, although negative findings have also been reported. Negative results have likewise been reported for cyproheptadine using the tail flick and hot-plate assay, but increased and decreased sensitivities to nociceptive stimuli have been demonstrated with other experimental procedures.

In a live rat model system, a serotonergic agonist (5MeODMT) which is known to cross the blood brain barrier decreased nociceptive responses in the hot plate, tail flick and shock titration assays. Yet, these effects were blocked by mianserin or metergoline only in the tail flick method. In spinalized rats, on the other hand, the opposite effects have been demonstrated.

Another serotonin agonist (8-OH-DPAT) has been shown to have no effect on nociceptive reflexes in the mouse tail flick assay, while producing hypo- or hyperalgesia in the hot plate and formalin bioassay. However, both analgesic and hyperalgesic effects of 8-OH-DPAT are observed when microinjected into the rat brain stem.

However, intrathecal serotonin has consistently been shown to produce analgesia which is blocked by methysergide and cyproheptadine and potentiated by fluoxetine in the tail flick assay but not in the hot plate assay.

Finally, classification of numerous molecular receptor sub-types for serotonin indicate both a duality (i.e., hyperalgesia vs. analgesia) and a redundancy of function.

3. Status of the Art

Rose et al. (Pharmacol. Biochem. Behav., 41: 219–226, 1991) hypothesize that excitable system agonist/antagonist combinations may be useful in the therapy of certain excitable system disorders. For example, Rose et al. hypothesize that combination therapy using nicotine/mecamylamine may be useful in the treatment of nicotine dependence and that methadone/naltrexone combined therapy might be employed in the treatment of heroin addiction.

Hamann et al. (Pharmacology Biochemistry & Behavior, 47: 197–201, 1994) teaches that at high doses, the hyperalgesic action of morphine is diminished and an analgesia was observed in rats. Additionally disclosed is that naltrexone produces analgesia that is diminished with increasing dose.

Hamann et al. (H. Pharmacol. Exp. Ther., 261: 707–715, 1992) discloses the analgesic effects of naltrexone and mecamylamine in rat brain sites exhibiting sensitivity to the hyperalgesic actions of (-)-nicotine and ethylketazocine. Both naltrexone and mecamylamine evoked dose-related analgesia when administered either intraperitoneally or by direct injection into active hyperalgesic brain stem regions. There is no teaching or suggestion of therapies in which both opioid and nicotinic antagonists, such as naltrexone and mecamylamine, are co-administered.

Hamann et al. (Pharmacology Biochemistry & Behavior, 43: 925–927, 1992) describe a dose related analgesia when lidocaine, cocaine, and bupivacaine were administered into the dorsal posterior mesencephalic tegmentum of conscious rats. There is, however, no mention of a combination therapy using opioid and nicotinic antagonists.

Rose et al. (Clinical Pharmacology and Therapeutics, July 1994) disclose the beneficial effect of mecamylamine in a combination therapy with a nicotine skin patch in the prolonged cessation of cigarette smoking.

Hamann et al. (Brain Research Bulletin, 29: 605–607, 1992) describes an apparent dose-related analgesic action of dynorphin A(1–13) antiserum when injected into the dorsal posterior mesencephalic tegmentum of conscious rats. Martin et al. (Society for Neuroscience Abstracts, 16: Abstract No. 267.7) describes the administration of 12 mecamylamine or naltrexone to Sprague Daily rats. When administered to the 4th ventricle, and mecamylamine antagonized the hyperalgesic effect of EKC and nicotine. There is again, however, no disclosure of naltrexone/mecamylamine combined therapy. Crain et al. (WO 95 03804) disclose a-method using co-administration of a bimodally acting opioid agonist and an excitatory opioid receptor antagonist for enhancing opiate analgesic potency or detoxifying an opiate addict.

In each of the above described publications, there is no suggestion to use combinations of two or more antagonists of excitable systems in the treatment of excitable system disorders. Moreover, there is no teaching or suggestion of combining opioid and nicotinic antagonists for treatment of excitable system abnormalities, particularly depression, drug abuse, and pain.

It is thus the present invention that for the first time provides methods for evaluating abnormalities in excitable system activity associated with psychopathologies and furnishes novel treatments with combinations of opioid, cholinergic, serotonergic and adrenergic antagonists. Application of excitable system activity compositions to the individuality of central nervous system processes which function in mediating and maintaining a balance in excitatory and inhibitory processes provides a new approach for the discovery of pharmacologic modalities which are devoid of abuse potential and are useful for the treatment of pain, drug abuse and underlying psychopathologies.

DISCLOSURE OF THE INVENTION

The invention provides compositions of nicotinic, opioidergic, serotonergic and adrenergic antagonists and methods of use thereof in the treatment of excitable system abnormalities, including pain, psychiatric disorders and drug dependence.

The invention further provides for compositions comprising a combination of at least two antagonists of different excitatory systems and use thereof in the treatment of excitable system abnormalities, pain and the like. Exemplary of the invention, is a combination of the opioid antagonist naltrexone and the nicotinic antagonist mecamylamine, as well as methods of using this combination in the treatment of excitable system disorders.

The invention also provides methods of treating excitable system abnormalities, pain and psychiatric disorders employing at least two antagonists of different excitatory cellular systems.

BRIEF DESCRIPTION OF DRAWINGS

FIGS. 11(A-1), 11(B-1), 11(A-2) and 11(B-2) show a comparison of antagonist modulation of naltrexone's anti-excitatory vs. inhibitory actions.

TABLE 1

Anatomical summary of microinjection experiments

| Desiation | Sterotaxic Coordinates | | Description of Surrounding Nuclei[b] |
|---|---|---|---|
| | AP[a] | Vertical | |
| VC | −4.3 | +2.4 | Above the solitary tract nuclei, medial longitudinal fasciculus and raphe obscuris nucleus |
| VM | −2.6 | +2.4 | Above the medial vestibular and gigantocellular reticular nuclei and below the medial cerebellar necleus |
| VR | −1.2 | +2.4 | Above the caudal pontine reticular nucleus, medial longitudinal fasciculus and gigantocellular reticular nucleus |
| A0.8 | −4.4 | +0.8 | Near the raphe obscuris and paramedian reticular nucleus |
| B0.4 | −1.2 | +0.4 | Near the raphe magnus, pontine reticular, and gigantocellular reticular nuclei. |
| C1.4 | −0.2 | +1.4 | Near the reticulotegmental and pontine reticular nuclei and above the raphe magnus and pontine reticular nuclei |

TABLE 1-continued

Anatomical summary of microinjection experiments

| Desiation | Sterotaxic Coordinates | | Description of Surrounding Nuclei[b] |
|---|---|---|---|
| | AP[a] | Vertical | |
| C3.0 | −0.2 | +3.0 | Near the central and pericentral dorsal tegmental nuclei within the dorsal medial tegmental area |
| D2.6 | +1.2 | +2.6 | Near rhaboid and paramedian raphe nuclei, between dorsal and median raphe nuclei, medial to pedunculopontine nuclei |
| E3.0 | +2.8 | +3.0 | Near the dorsal tegmental decussation within the central tegmental tract |
| E1.0 | +2.8 | +1.0 | Near the ventral tegmental area within the interpeduncular nuclei |
| E4.4 | +2.8 | +4.4 | Within the central gray near the aqueduct |

[a]Anterior posterior axis of rat brain.
[b]Descriptions derived from sagittal and coronal sections provided by Paxinos and Watson (1986). Nuclei described are within an approximate 1 mm radius from the estimated sites of microinjection.

Figure 19:
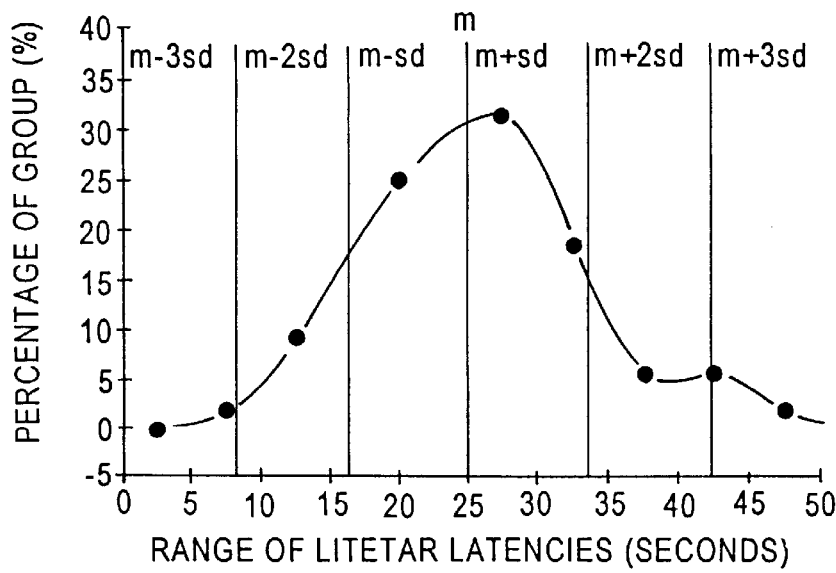

FIG. 19 shows the distribution of TAR response latencies in female sprague-daily rats.

DETAILED DESCRIPTION OF THE INVENTION

The present invention, together with the therapies and pharmacological products which are described herein, are based on the relationships developed in Provisional U.S. patent application entitled "Operations of Excitable Systems", the disclosure of which is incorporated in its entirety herein by reference.

Human and animal investigations have contributed to an understanding of drug withdrawal abstinence syndromes and maladaptive feeling states (hypophoric states). Studies in rats, dogs, and man have helped to delineate many important characteristics of these syndromes including 1) personality structure of patients with addictive diatheses; 2) reinforcing properties of drugs of abuse; 3) physiologic adaptations during abstinence from chronic drug exposure; and 4) increased nociceptive reactivity during abstinence.

Figure 1A:
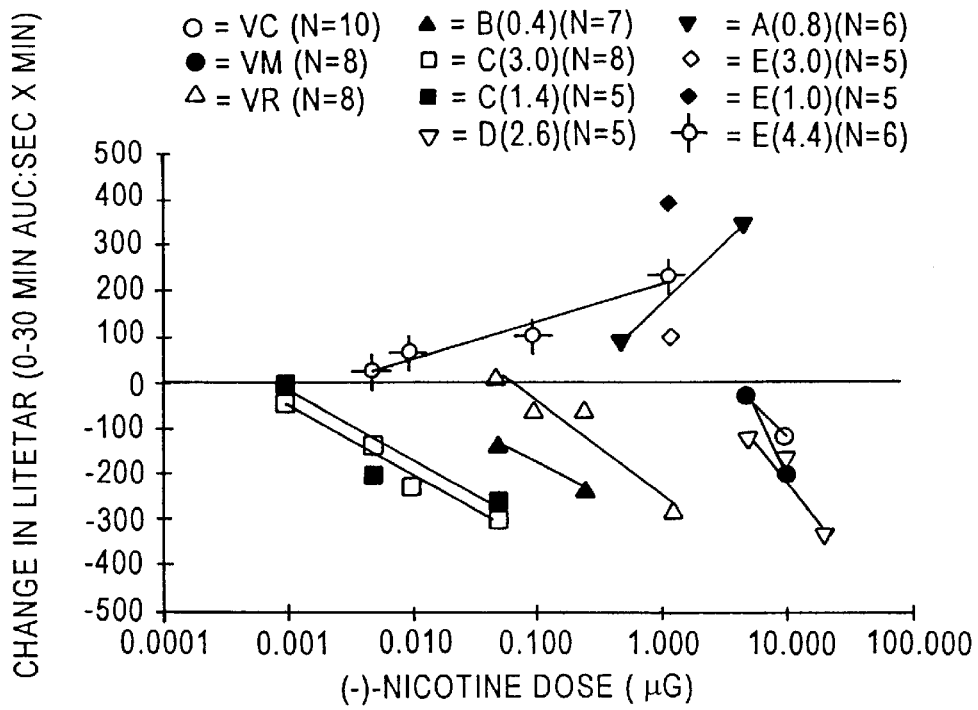
FIGS. 1(A) and 1(B) depict a comparison of the linear portions of the dose-nociceptive-response lines (LITETAR) from several brain sites for (−)-nicotine (A) and ethylketazocine (EKC) (B). (Brain cites described in Table 1.)
Figure 1B:
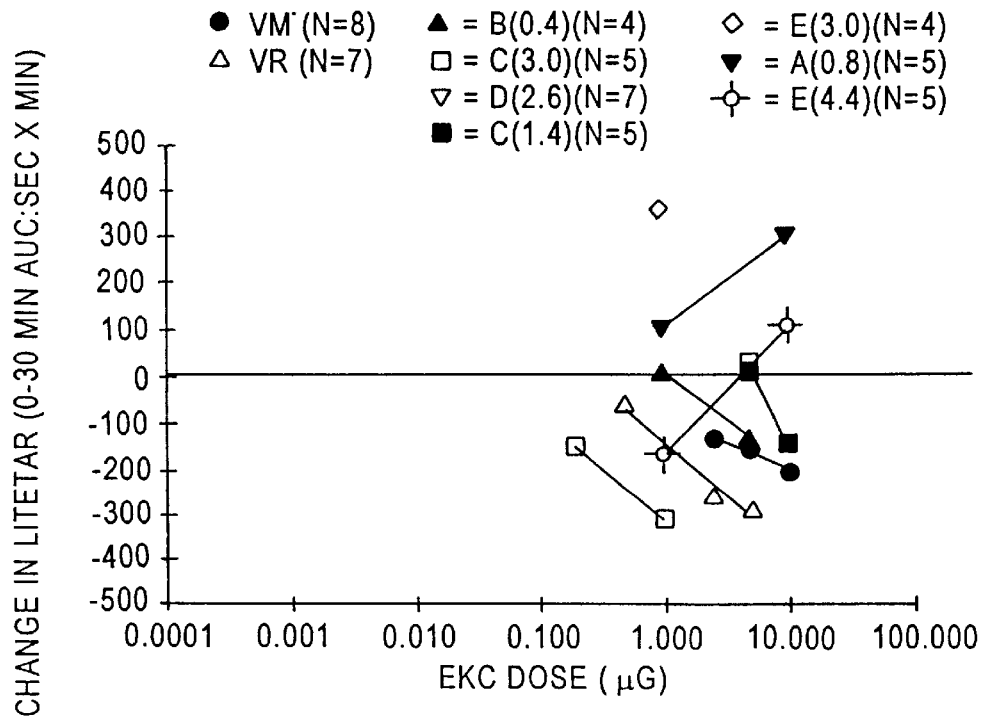
Figure 2:
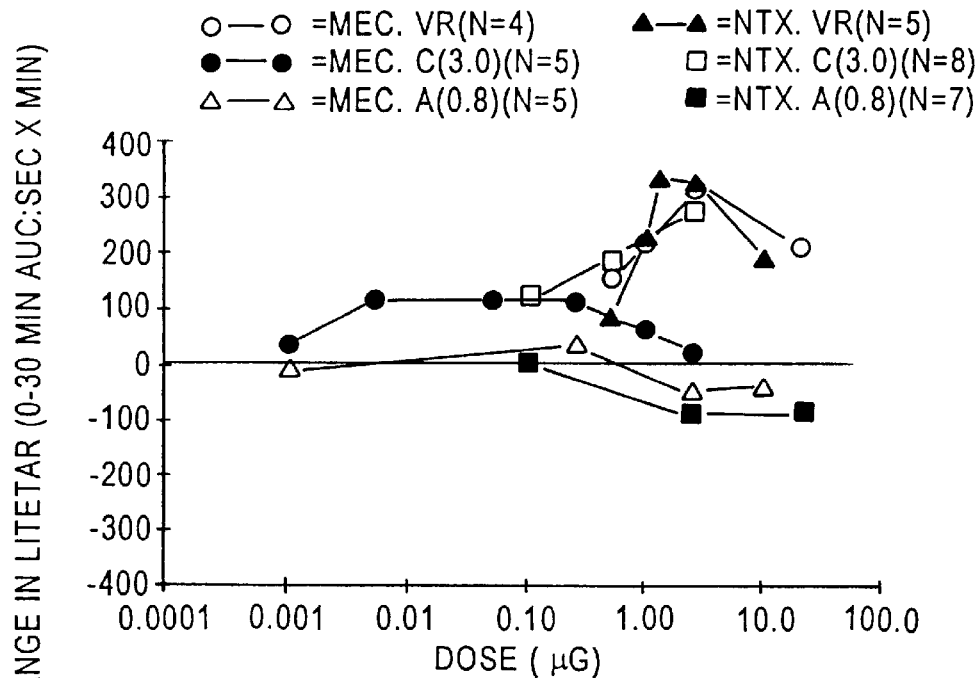
FIG. 2 depicts the effects of naltrexone (NTX) and mecamylamine (MEC) at active excitatory (hyperalgesic) and inhibitory (analgesic) brain stem sites.
Figure 3:
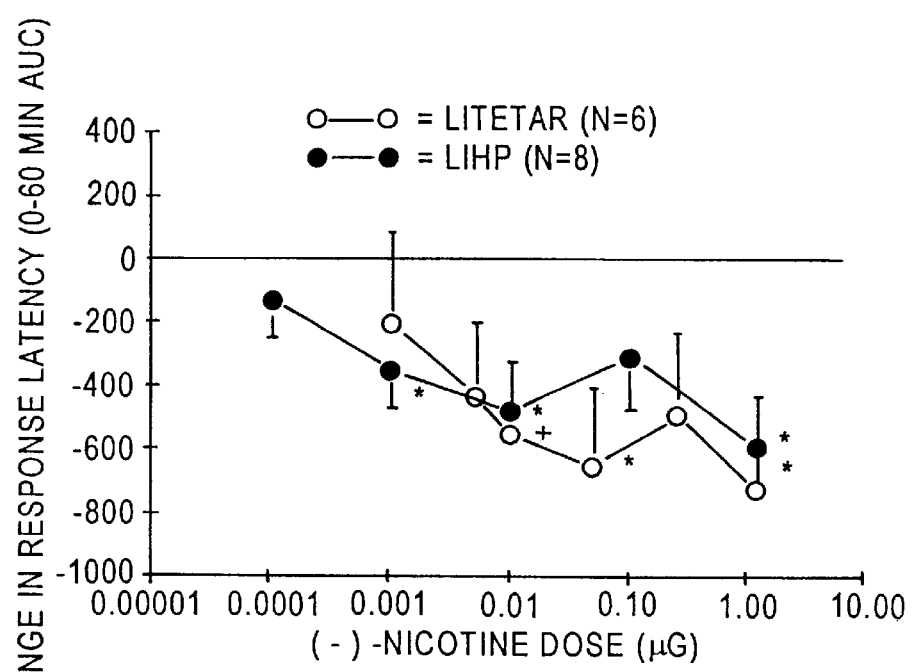
FIG. 3 provides a comparison of the effects of (−)-nicotine administered in the DPMT (C3.0) of rats by using the tail avoidance (TAR) and hot plate (LIHP) assays.
Figure 4:
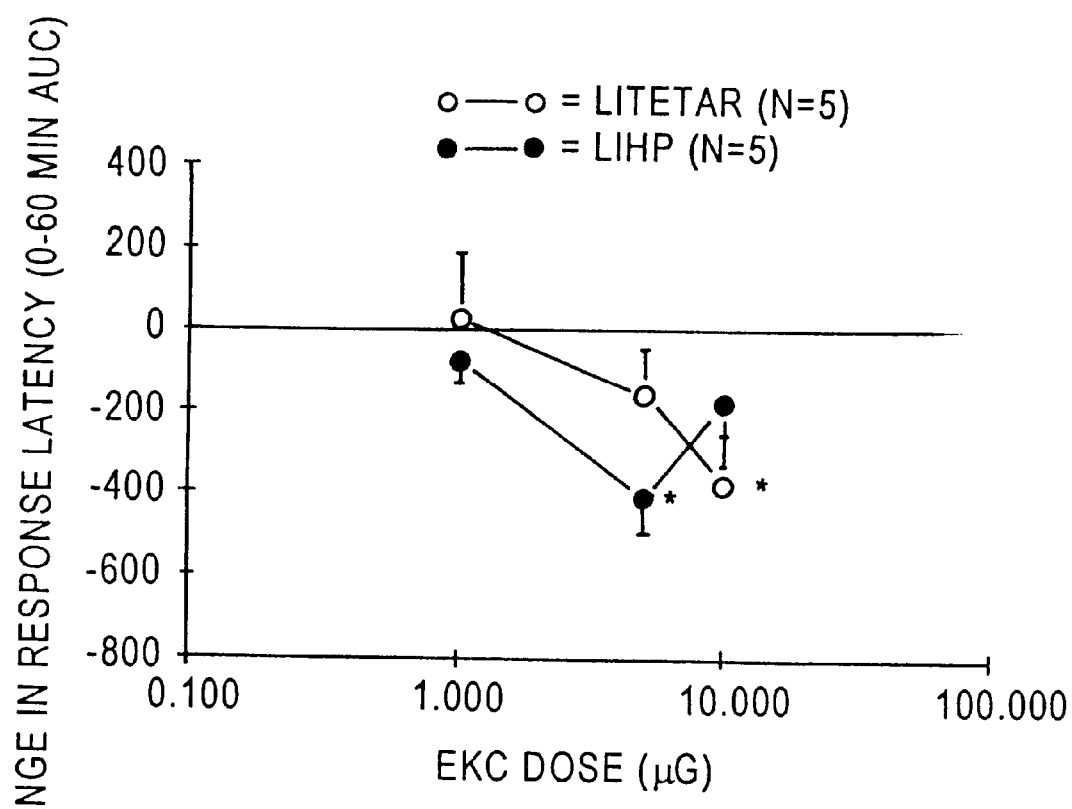
FIG. 4 provides a comparison of the effects of ethylketazocine (EKC) administered into the DPMT (C3.0) of rats by using the-TAR and LIHP assays.

Studies of the present inventor have been concerned with the excitatory (hyperalgesic) nociceptive processes of the central nervous system. Opioid and nicotinic excitatory (hyperalgesic) processes have been identified in the brain stem of rats from the middle of the fourth ventricle to the dorsal posterior mesencephalic tegmentum (Table 1, FIG. 1). In FIG. 1, a comparison of the linear portions of the low-intensity thermally evoked tail avoidance response (LITETAR) dose response from several brain sites for (−)-nicotine (A) and ethylketazocine (EKC)(B) are provided. The lines shown are calculated regression lines. Each value is the 0–30 minute area under the curve (AUC), and "n" is the number of rats used in the study of the site. These data indicate the presence of opioid and nicotinic excitatory (hyperalgesic) processes in the brain stem from the mid-fourth ventricle to the dorsal posterior mesencephalic tegmentum (DPMT). FIG. 2 depicts the effects of naltrexone (NTX) and mecamylamine (MEC) at active excitatory (hyperalgesic) and inhibitory (analgesic) brain stem site in the rat. When naltrexone and mecamylamine were microinjected into the DPMT (C3.0) and rostral to the fourth ventricle (VR), dose related analgesia was produced. These data support the presence of tonically active excitatory processes in the brain stem. Thus, these excitatory processes are extremely sensitive to (−)-nicotine and ethylketazocine (EKC) and appear to exhibit tonic activity since naltrexone and mecamylamine exhibit anti-excitatory actions when microinjected into brain stem loci (FIG. 2). Several studies have been performed which demonstrate different characteristics of these opioid and cholinergic excitatory processes. Excitatory actions of (−)-nicotine (FIG. 3) and EKC (FIG. 4) have been demonstrated using both tail avoidance reflex (TAR) and hot plate assays. (In FIG. 3, the effects of (−)-nicotine administered into thee DPMT (C3.0) of rats as measured by TAR and LIHP assays are compared, whereas these assays are compared for ethylketazocine in FIG. 4.)

Figure 5A:
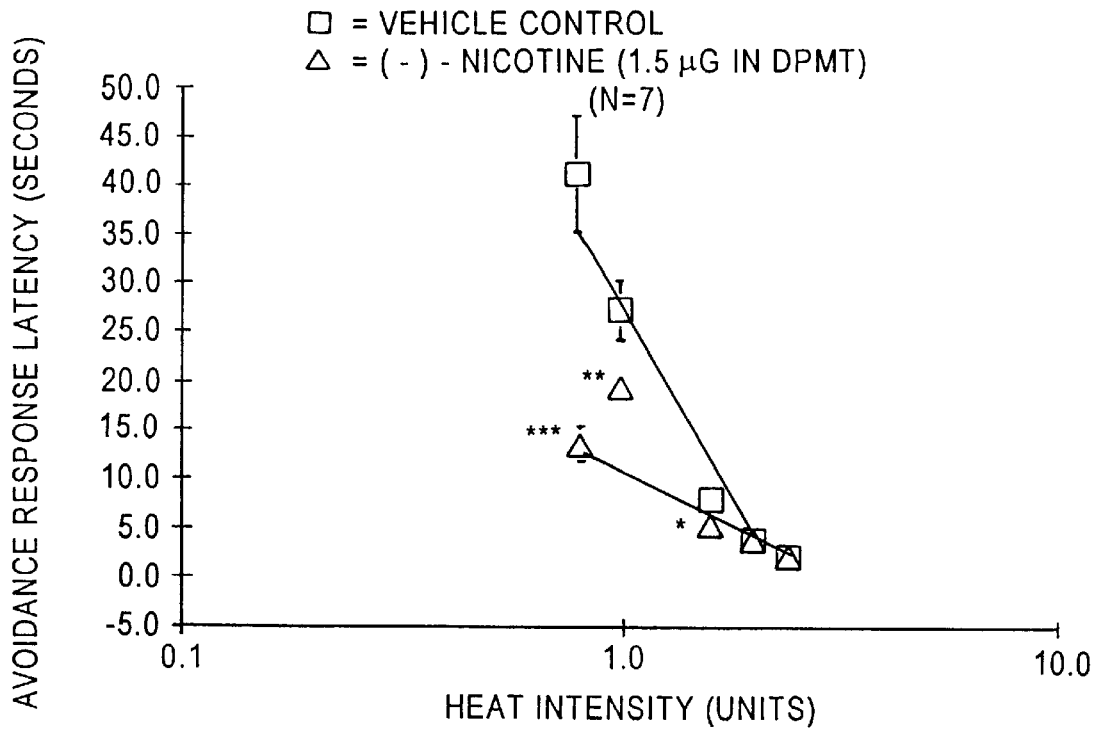
FIGS. 5(A) and 5(B) depict the effects of 1.5 ug (−)-nicotine administered into the DPMT on the latency to onset (A) and magnitude (angular displacement) (B) of TARs in rats treated with 15 mg/kg pentobarbital.
Figure 5B:
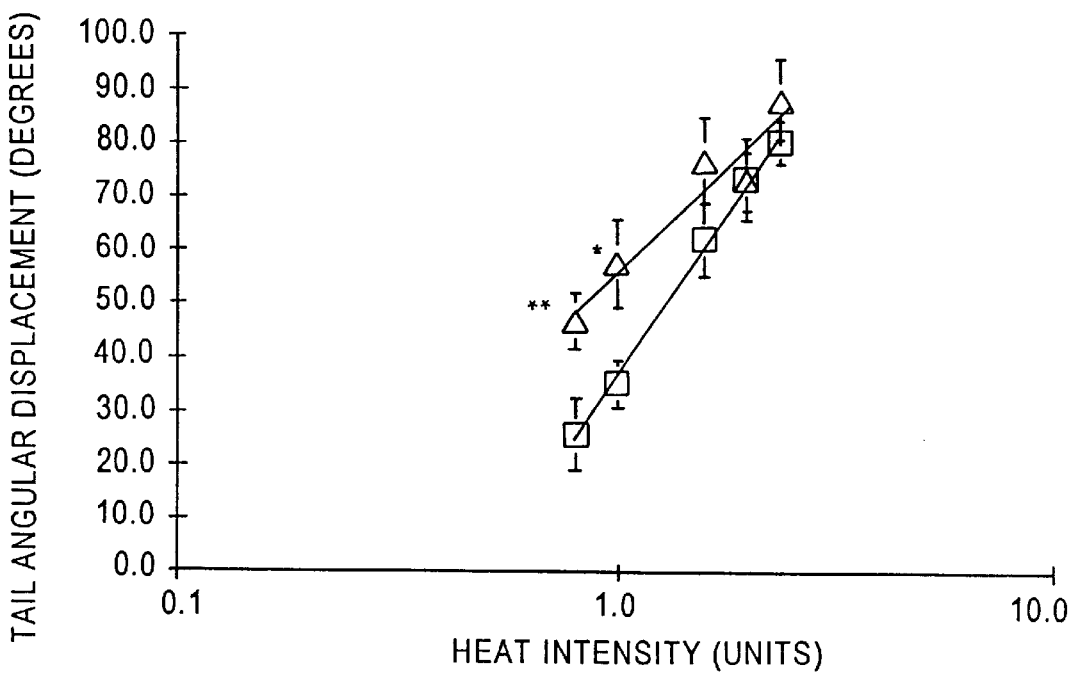
Figure 6:
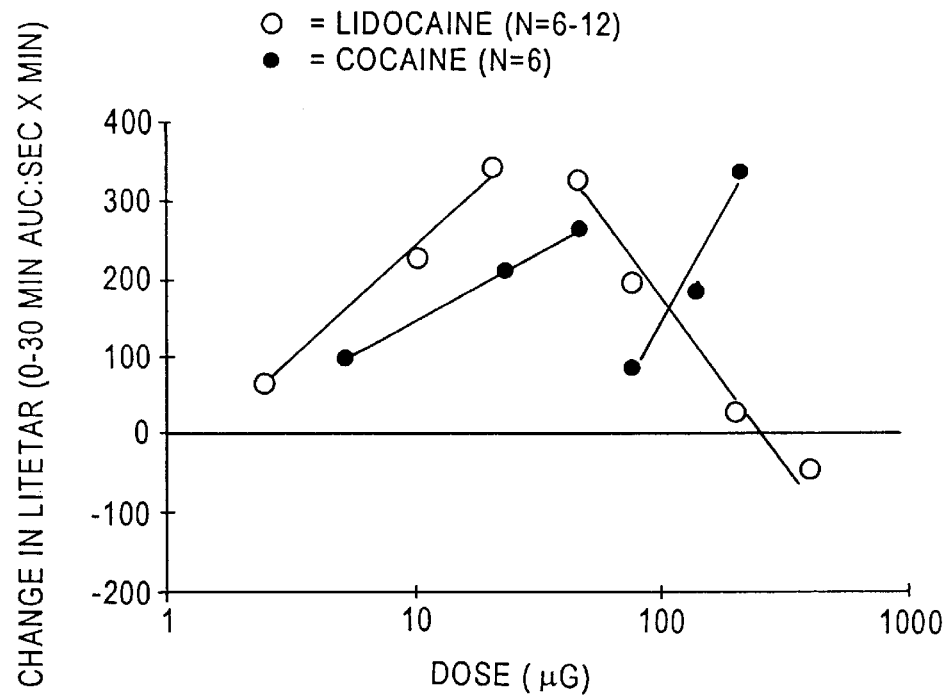
FIG. 6 provides a comparison of the linear portions of the dose-nociceptive-response curves for lidocaine and cocaine when micro-injected into the rat brainstem (DPMT) excitatory sites.
Figure 7:
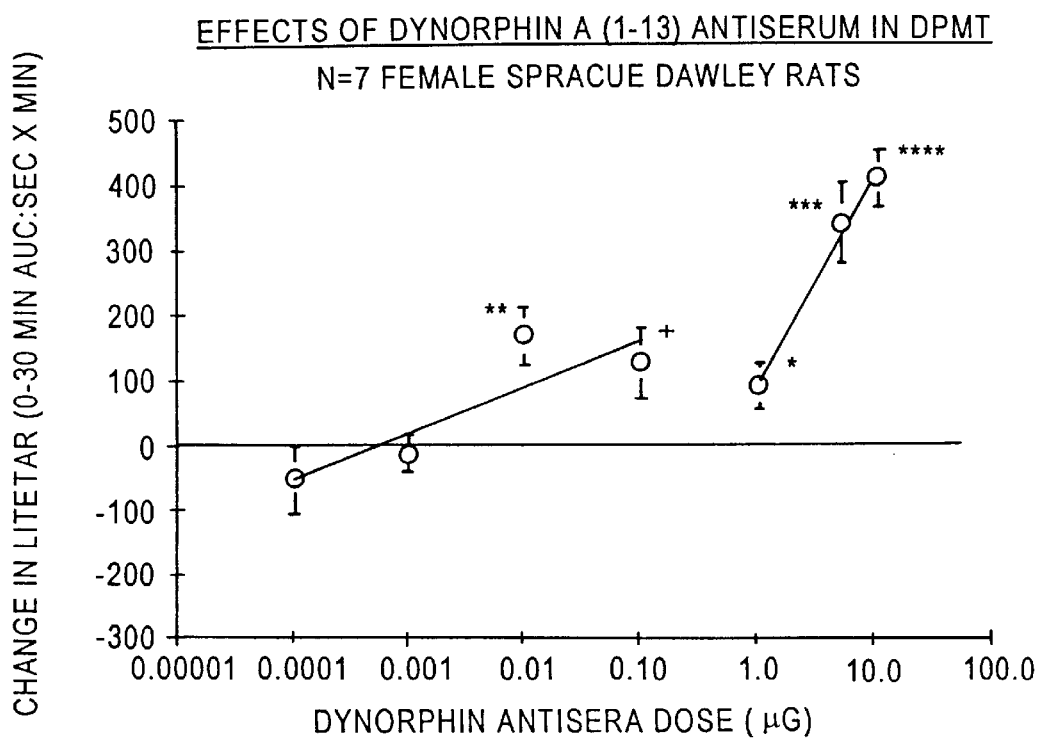
FIG. 7 provides a comparison of portions of the dose-nociceptive-response curve for Dynorphin A(1–13) antiserum in the dorsal posterior mesencephalic tegmentum (DPMT).
Figure 8:
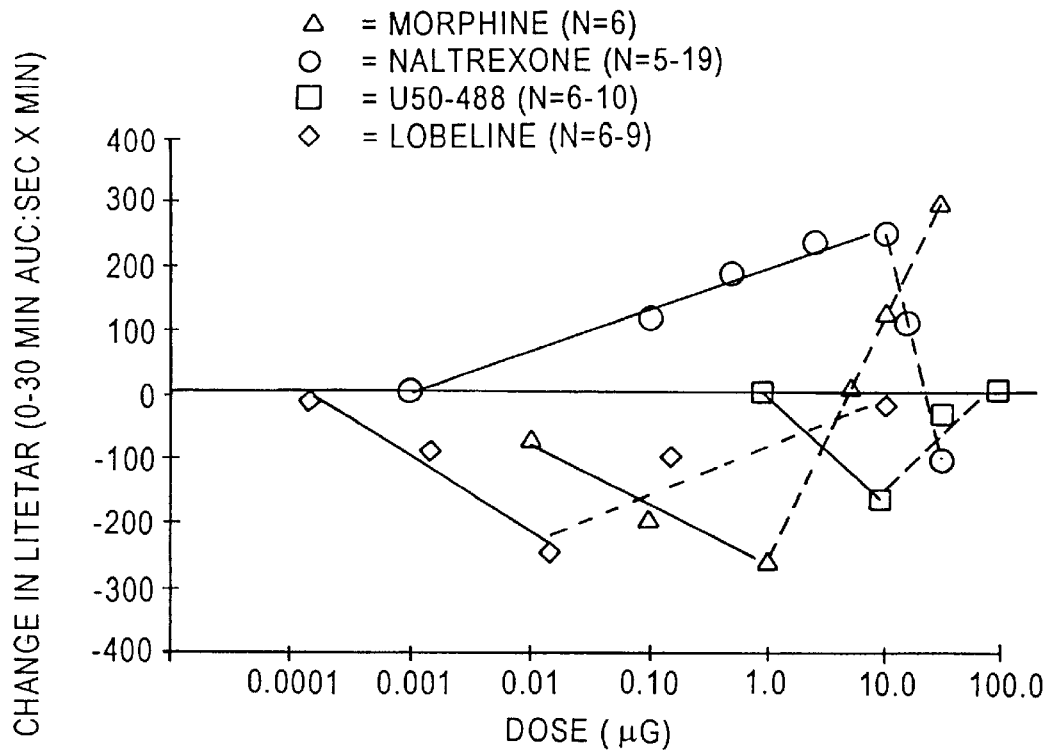
FIG. 8 depicts a dose-response curves for morphine naltrexone, U50-488, and (−)-lobeline when graded doses were administered into the dorsal posterior mesencephalic tegmentum (DPMT).

Activation of excitatory nicotinic processes in the DPMT changes the slope of the stimulus response relationships for both latency (FIG. 5A) and magnitude (angular displacement; FIG. 5B) of the thermally evoked tail avoidance response. These data support the notion that modulation of brain stem excitatory processes can modify excitable system activity. Lidocaine and cocaine exhibit biphasic dose response curves when microinjected into the DPMT (FIG. 6). FIG. 6 provides evidence for anti-excitatory and excitatory actions of cocaine, as well as anti-excitatory and anti-inhibitory actions of lidocaine in DPMT, and tonic excitatory activity and different modulation of excitable system activity for cocaine and lidocaine. Dynorphin A (1–13) antibody (FIG. 7) and several opioid drugs (FIG. 8) also exhibit biphasic dose response curves when microinjected into the DPMT, providing evidence for concentration dependent dynorphin excitatory functions in the brain stem and that the extremely sensitive opioid and nicotinic excitatory processes in the DPMT are colocalized with less sensitive inhibitory processes.

Figure 9:
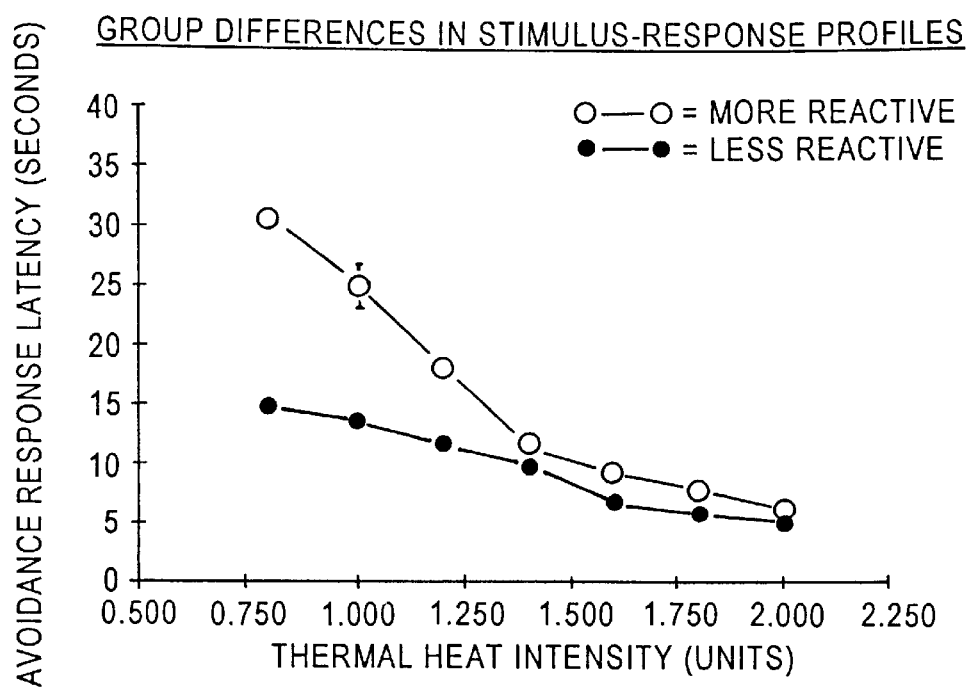
FIG. 9 is a comparison of thermal stimulus response curves for rats with different nociceptive reactivity. (●=more reactivity; ○=less reactivity)
Figure 10:
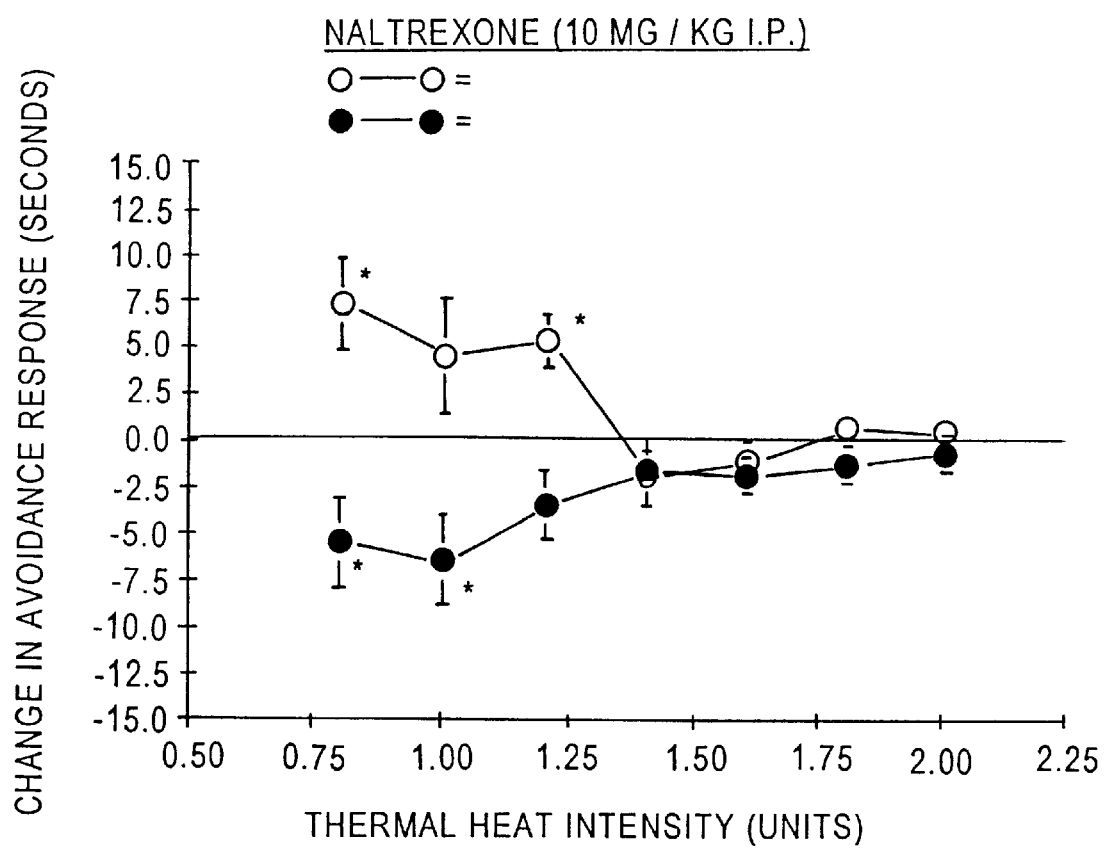
FIG. 10 shows a comparison of the effects of naltrexone on excitable system activity for rats with different nociceptive reactivity. (○=more reactivity; ●=less reactivity)
Figure 12:
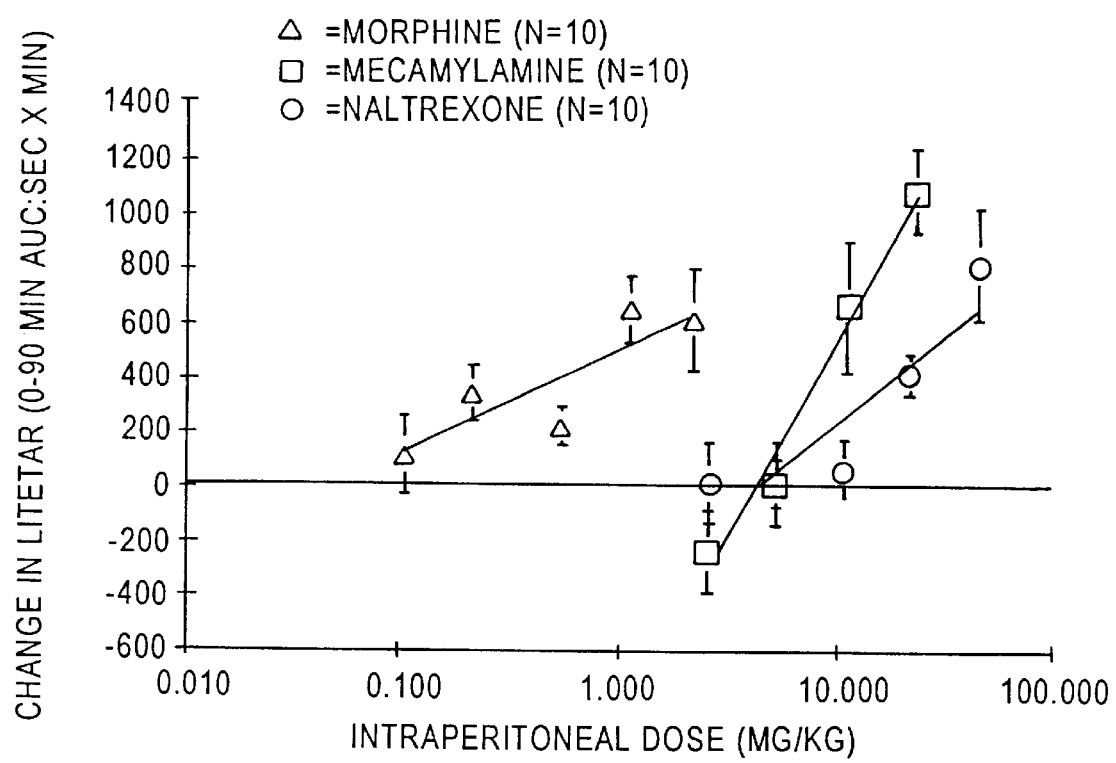
FIG. 12 shows the effects of intraperitoneal naltrexone and mecamylamine on the latency of the TAR as compared to morphine.
Figure 13A:
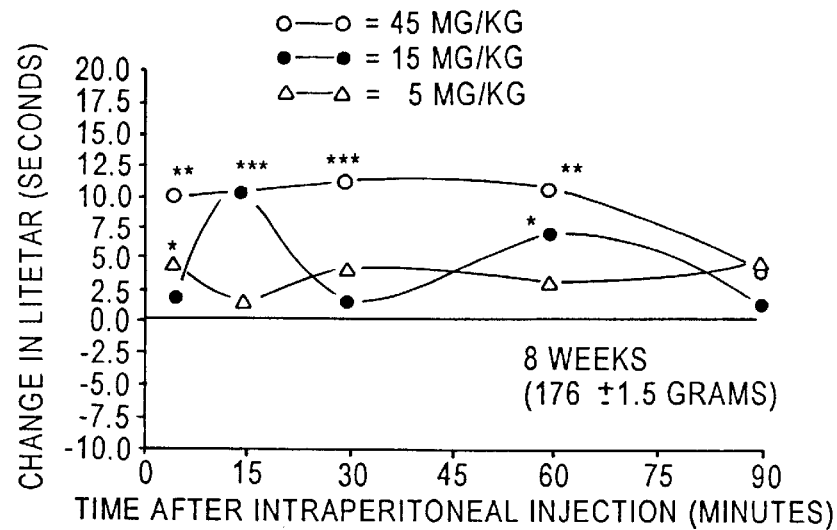
FIGS. 13(A)–13(E) depict the time action relationships for naltrexone's analgesic/hyperalgesic actions when given to female rats at 8, 12, 19 and 39 weeks of age.
Figure 13B:
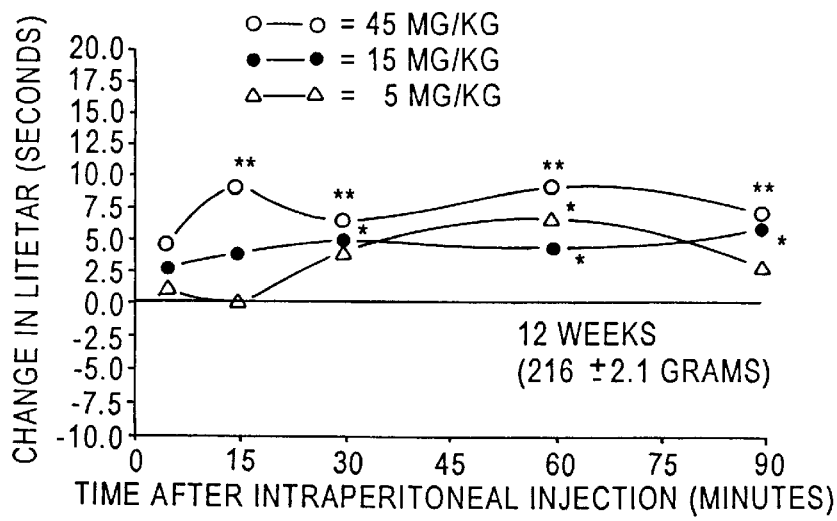
Figure 13C:
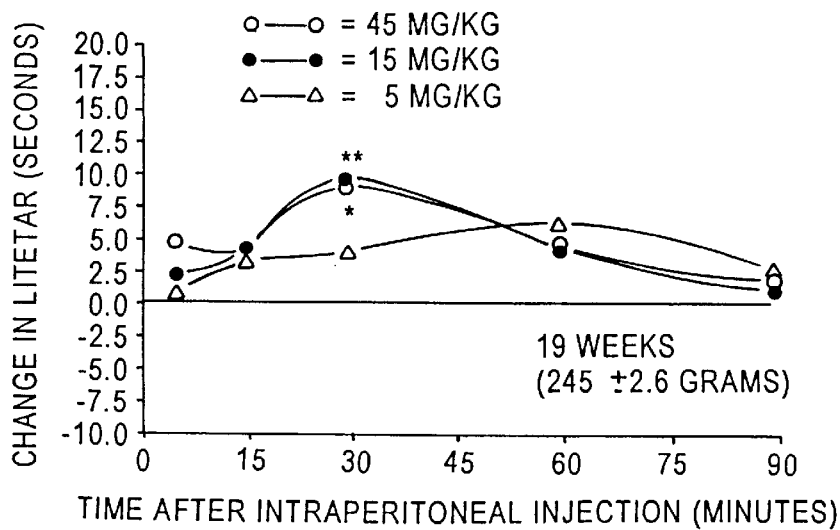
Figure 13D:
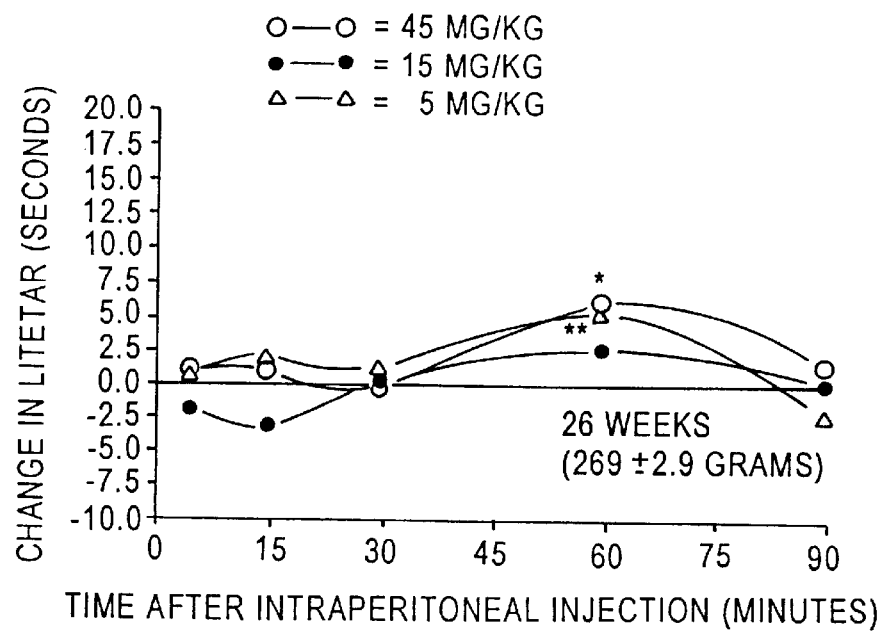
Figure 13E:
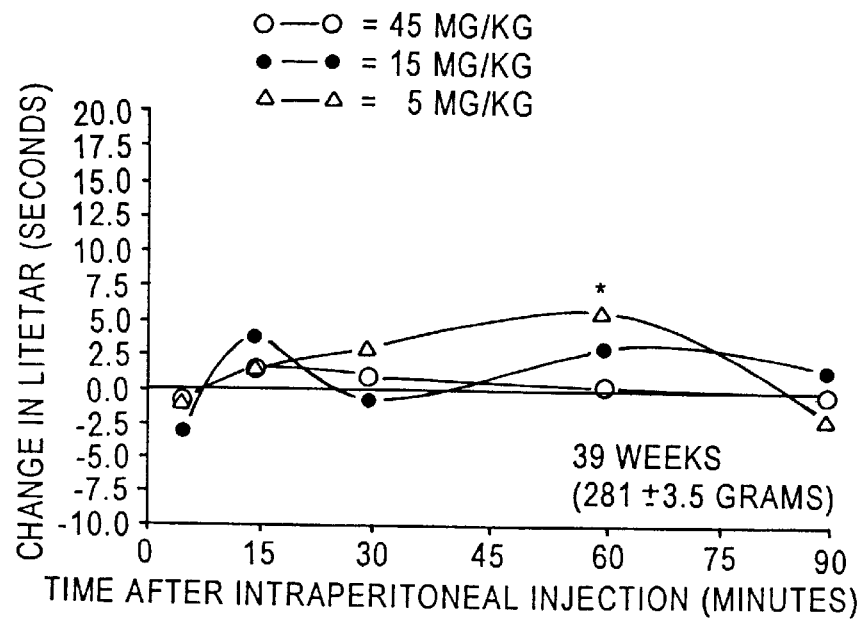
Figure 14A:
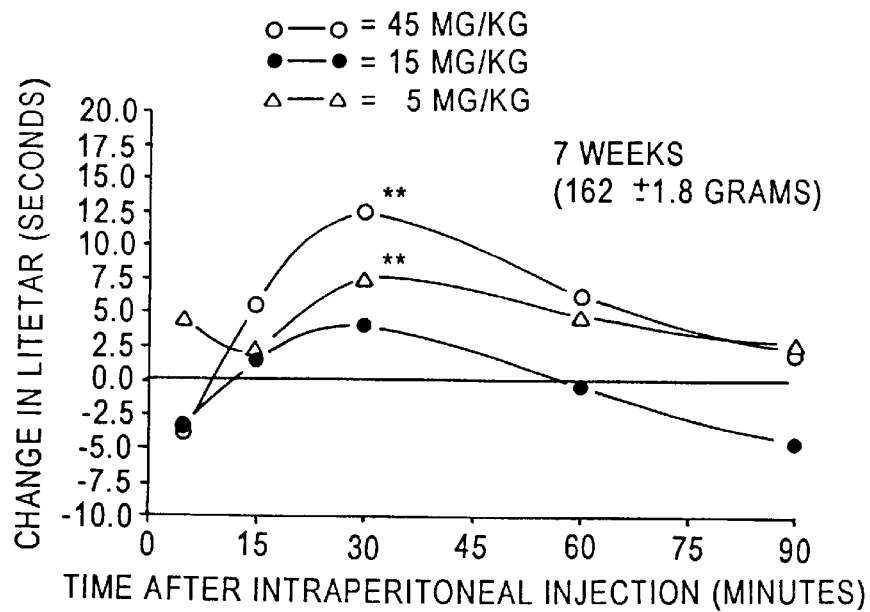
FIGS. 14(A)–14(D) depict the time action relationships for naltrexone's analgesic/hyperalgesic actions when given to female rats at 7, 10, 20 and 40 weeks of age.
Figure 14B:
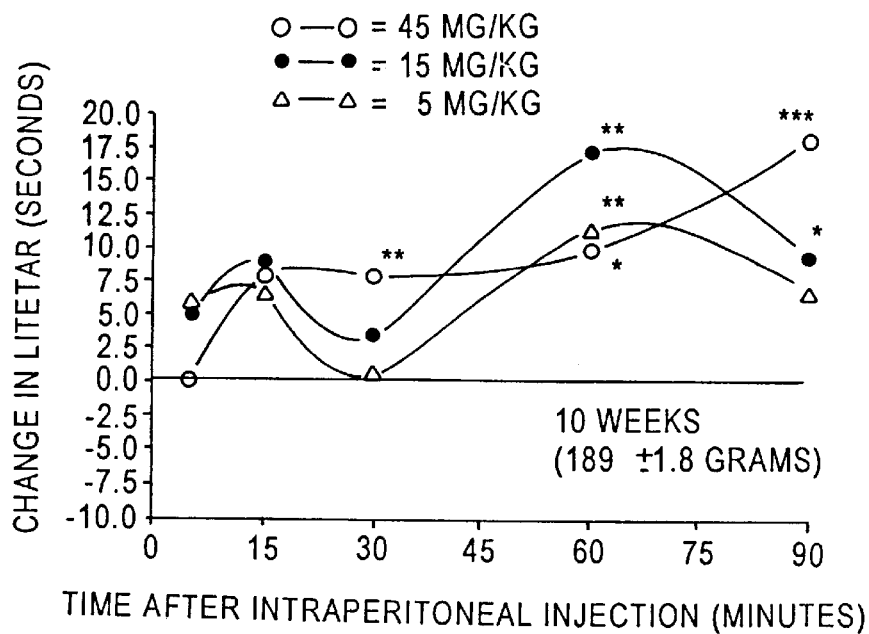
Figure 14C:
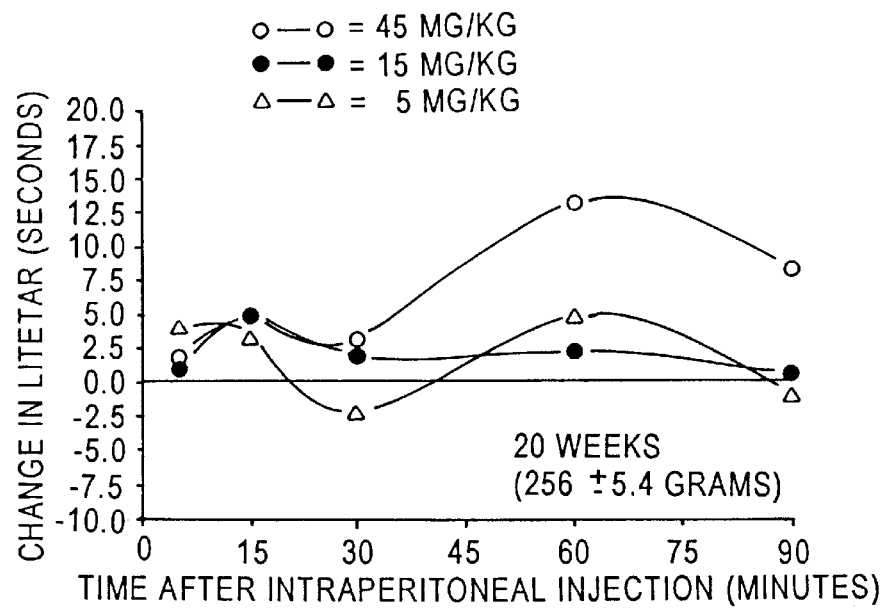
Figure 14D:
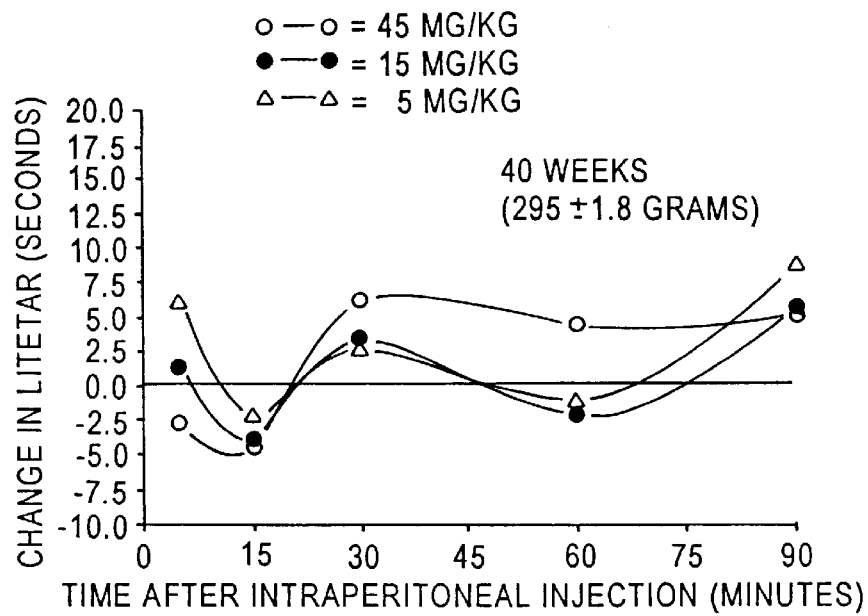
Figure 15A:
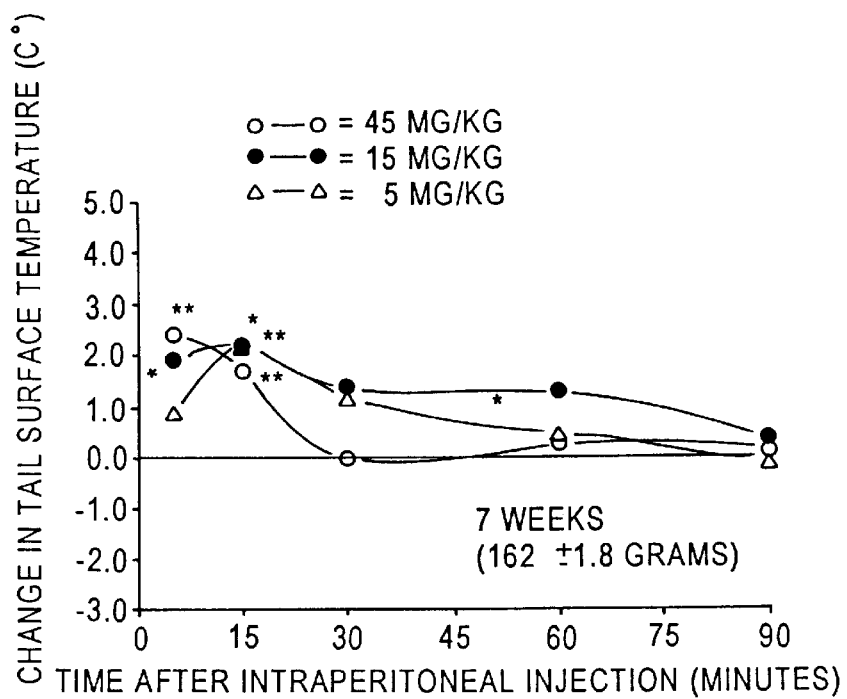
FIGS. 15(A)–15(D) depict the time action relationships for naltrexone's actions on tail surface temperatures when given to female rats at 7, 10, 20 and 40 weeks of age.
Figure 15B:
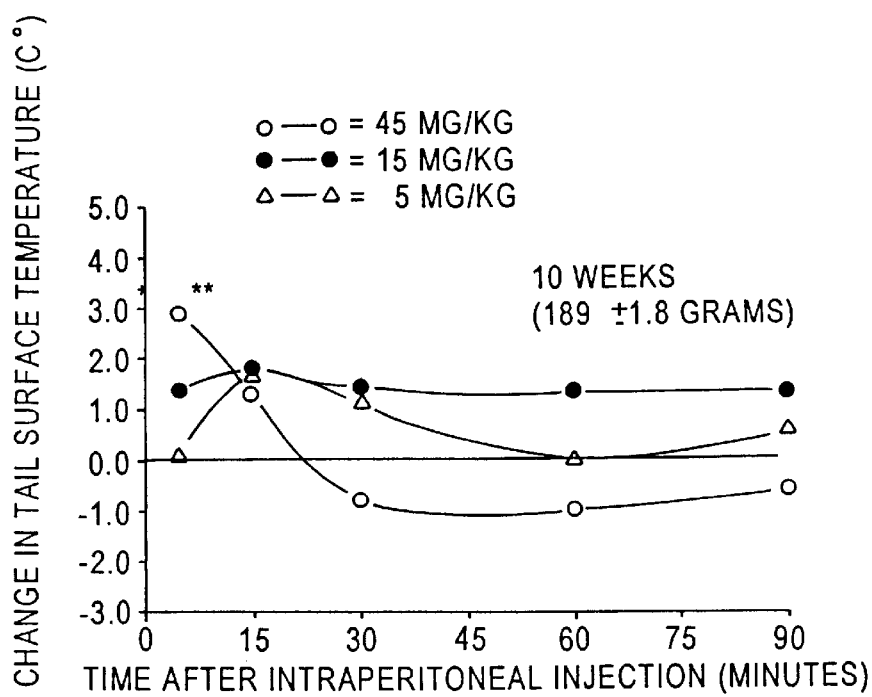
Figure 15C:
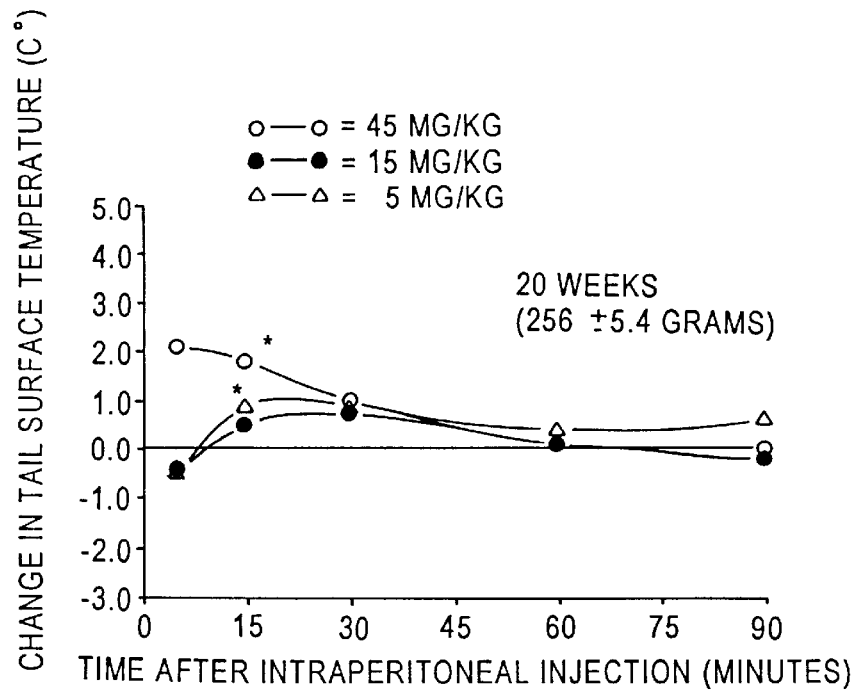
Figure 15D:
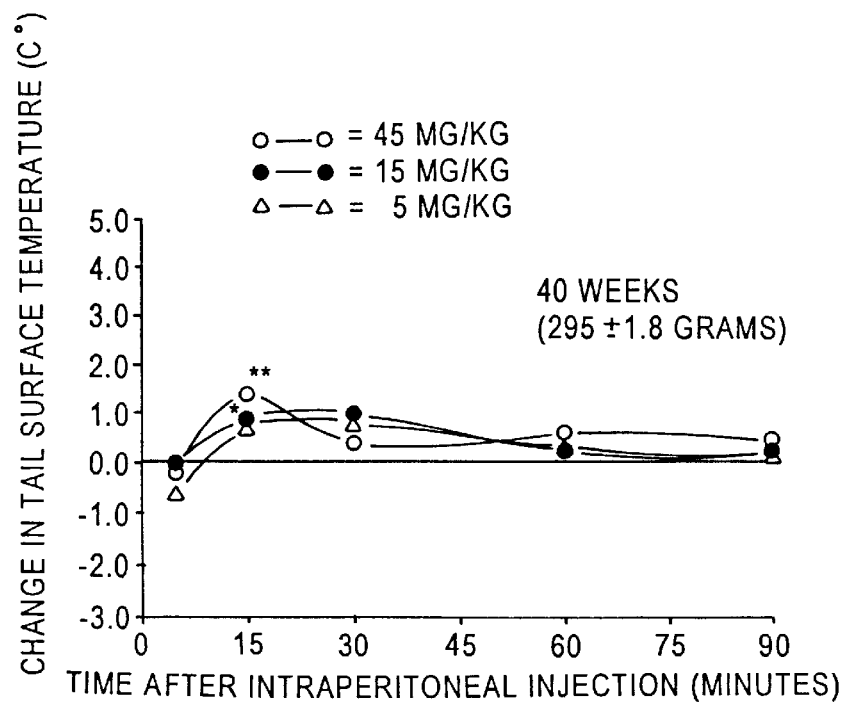

During the study of excitatory and inhibitory processes, the present inventor observed considerable variation between test animals in the response to both nociceptive stimuli and pharmacologic interventions. Thermal stimulus response relationships, which reflect excitable system activity, exhibit different patterns (FIG. 9), which suggests differences in individual excitable system activity. Single doses of naltrexone have no effects in nociceptive assays which use higher intensity thermal stimuli but have different effects when animals are exposed to lower intensity thermal stimuli. These differing effects depend upon the nociceptive reactivity of the individual animals (FIG. 10) as well as previous drug exposure history. Similar paradoxical results with regard to intensity of the thermal stimulus used to elicit the thermally evoked nociceptive reflexes have been obtained with nicotinic (mecamylamine), serotonergic (methysergide) end adrenergic (phentolamine) antagonists. Modulatory actions of these antagonists on the excitatory and inhibitory action of naltrexone (FIG. 11) have also been detected.

Figure 16:
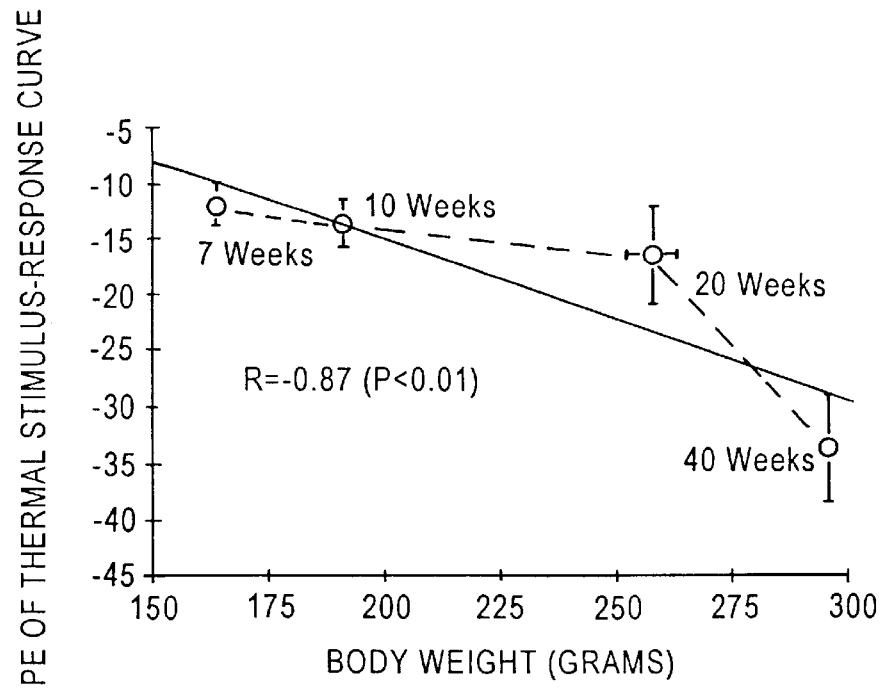
FIG. 16 shows the relationship between rat weight (age) and the negative slope of the thermal stimulus response curves.

The influences of age and excitable system activity, as measured by individual nociceptive reactivity, on the analgesic actions of naltrexone have also been evaluated. In one experiment, time action data showed significant ($P<0.05$–$P<0.001$) analgesic actions of naltrexone which decreased with age (FIG. 13). Hyperalgesic responses were observed in several older (20–40 weeks) animals. In a second study similar results revealed that the analgesic actions of naltrexone decreased with increasing age (FIG. 14). Again, hyperalgesic actions of naltrexone were observed in several older animals. Naltrexone produced a transient increase in tail surface temperature which was most prominent in younger rats (FIG. 15). Thermal stimulus nociceptive-response studies (FIG. 16) revealed highly significant (P<0.001) regression of between stimulus variation for each age group. The negative slope of the stimulus response relationships increased in steepness with rat age. These experiments demonstrate that the effects of naltrexone on nociception may change with age, and are most demonstrable in younger animals when nociceptive reactivity is enhanced.

To summarize the above, the present inventor has demonstrated brain stem opioidergic and nicotinic excitatory (hyperalgesic) processes which exhibit tonic activity. These processes co-vary somewhat throughout the brain stem with excitatory processes most sensitive in the posterior dorsal mesencephalic tegmentum.

A number of drugs of abuse including nicotine, morphine and cocaine have been shown to have effects on brain excitatory processes. The invention thus provides methods for detecting and comparing individuality in excitable system activity using nociceptive responses and drug effects. Clinical studies have suggested that the analgesic and hyperalgesic actions of opioid antagonists were most common in placebo reactors. These observations may be explained by viewing the actions of opioid antagonists as being related to the individual pain reactivity and that certain subjects have a greater tendency toward mobilizing endogenous inhibitory and/or excitatory opioid peptides. The present invention thus provides pharmaceutical compositions which are useful in treating abnormalities of excitable system activity related to exaggerated excitatory and nociceptive reactivity.

An individual's excitable system activity is thought to arise from a balance between opposing inhibitory and excitatory processes. This balance between opposing forces is due to redundant endogenous cellular receptors and neurochemical processes which are determined by multiple alleles and exhibit a biological distribution approximating a normal distribution (FIG. 19). Under the practice of the present invention, the individual "outliers" can be determined and their excitable system activity altered by inhibiting the excitatory processes described.

The control response attributable to endogenous neurotransmitter mechanisms acting to produce excitable system activity are represented by the expressions in FIG. 19, where inhibitory and excitatory represent opposite phenomenology that in combination produce a given state of excitable system activity. The subscript identifies the transmitter-receptor type or sub-type, "e" is the activity of the endogenous agonist for opposing systems X and Y, Rt is the total number of the receptor sub-type and Kx and Ky are the dissociation constants of the endogenous agonist for opposing systems.

Since it is known that several endogenous receptor-neurochemical systems operate through regulatory G-proteins, modifications of the compositions of excitable system activity which include a regulatory protein term are also disclosed. This invention uses the relationship disclosed in Table 2, as well as the slope of log stimulus response relationships, to represent the activity of excitable systems, which activity can then be altered by the compositions of the present invention.

While it is currently not clinically practical to determine exact values for pharmacologic components of excitable system activity, knowledge of the in vivo characteristics of opposing inhibitory and excitatory influences, together with knowledge of nociceptive reactivity, allow for clinical application of the combination compositions disclosed herein.

Determination of the slope of the log-stimulus log-nociceptive response relationship provides an estimate of excitable system activity. The relative ratio of inhibitory and excitatory processes determine this estimate. Individuals having a shallow slope (i.e., more excitatory function) or extremely steep slope (i.e., excess inhibitory function) may be viewed as having enhanced or diminished excitability and sensation of nociceptive stimuli. Those individuals who exhibit extremes in excitable system activity are considered under the invention to be predisposed to pain and psychiatric syndromes. This invention uses compositions of excitable system activity and the knowledge of excitatory opioid, cholinergic, serotonergic and adrenergic excitatory processes to treat such syndromes. These compositions include those clinical interventions which will modify the individual's excitable system activity, in particular treatments with pharmacologic and physiologic antagonists of excitable system cellular receptor systems. Accordingly, this invention provides for pharmaceutical products containing combination of opioid, cholinergic, serotonergic and adrenergic antagonists, preferably as a combination of antagonists for two distinct excitable system cellular receptors systems.

Figure 17:
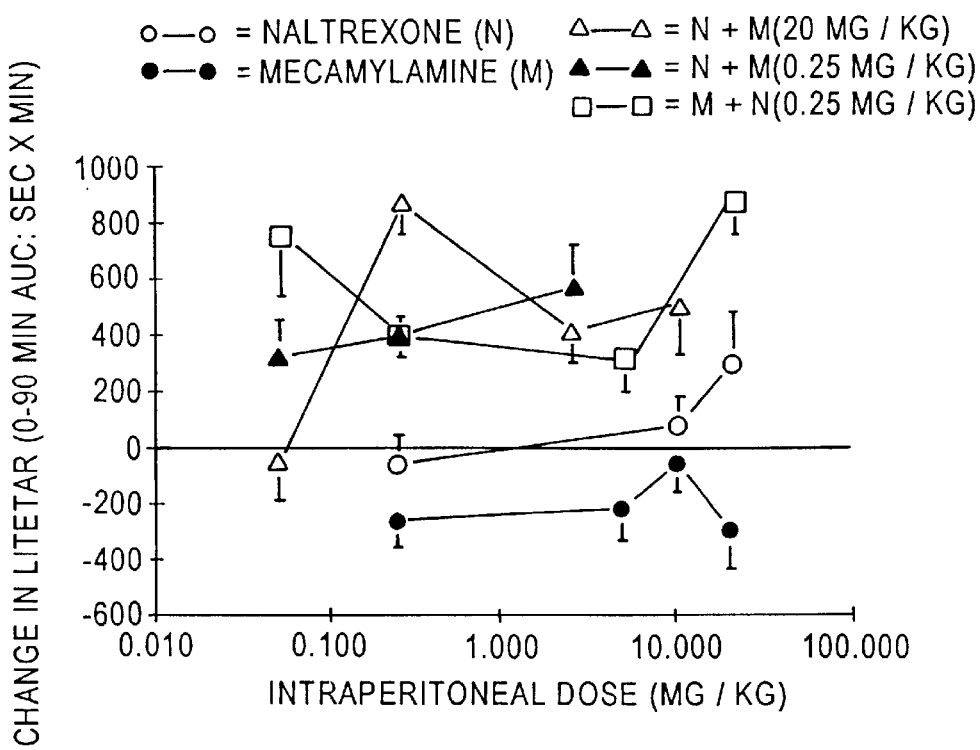
FIG. 17 shows a comparison of anti-excitatory (analgesic) of naltrexone and mecamylamine combination intraperitoneal doses.
Figure 18:
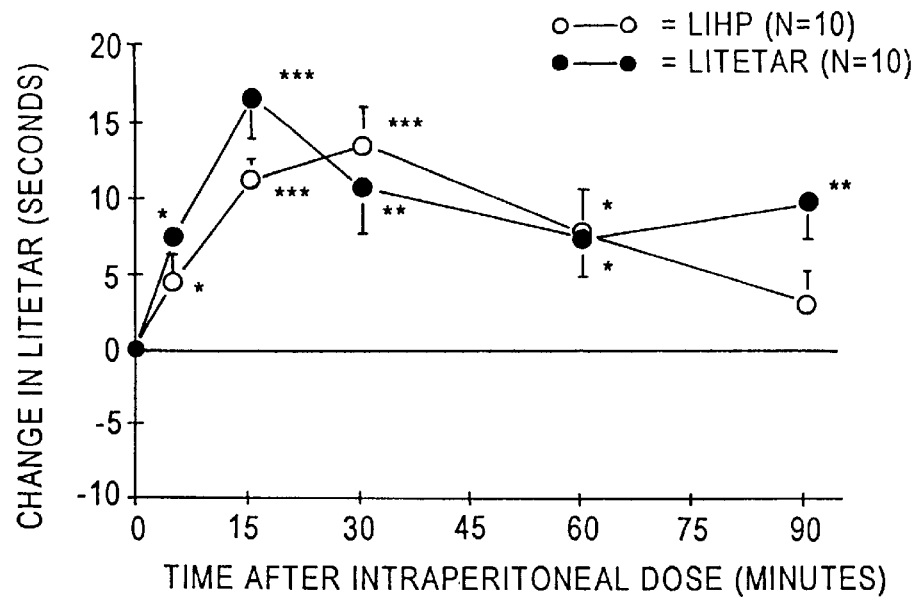
FIG. 18 provides a comparison of time action curves for the analgesic (anti-excitatory) actions of naltrexone (0.25 mg/kg) and mecamylamine (0.25 mg/kg) on the TAR and low intensity hot plate assay.

As shown in FIGS. 17 and 18, the combination of naltrexone and mecamylamine has anti-excitatory action when combined in extremely low doses. FIG. 17 compares the inhibitory actions of naltrexone and mecamylamine combinations in intraperitoneal doses. Highly significant analgesia was produced with the very low doses of naltrexone and mecamylamine. FIG. 18 compares the time actions curves for the analgesic (inhibitory) actions of naltrexone (0.25 mg/kg) and mecamylamine (0.25 mg/kg) on nociception using the TAR and low-intensity hot plate assay. In viva experimental evidence thus demonstrates that combination of low doses of naltrexone and mecamylamine exert anti-excitatory actions.

According to the provisional U.S. Patent application entitled "Operations of Excitable Systems", modulation of excitable system activity may be induced either pharmacologically or physically, or both. The present invention provides for novel pharmacologic therapies which include opioid antagonists in different combination with 1) nicotinic antagonists; 2) serotonergic antagonists; 3) adrenergic antagonists. Such combinations are anticipated to be particularly useful in the treatment of drug dependence.

The invention further provides compositions of excitable system activity which may be used in therapies for individuals with enhanced or reduced excitatory function by altering the activity of excitatory processes. Thus, practice of the invention may include the use of one or more agonists of excitable and inhibitory systems.

The invention further includes methods to increase or decrease excitable system activity as indicated by it's numeric value (Table 2) and thus alter the state of the excitable system away from the maladaptive psychiatric dimensions associated with enhanced or diminished nociceptive reactivity.

Opioid antagonists useful in the practice of the invention include (but are not limited to): naltrexone, naloxone, beta-flunaltrexamine, binaltorphimine and norbinaltorphamine, and nalmafene.

Nicotinic antagonists useful in the practice of the invention include (but are not limited to): mecamylamine, beta-erythroidin, hexamethonium and pempidine.

Serotonergic and/or adrenergic antagonists useful in the practice of the invention include (but are not limited to) anti-depressant drugs currently available for clinical use, including methysergide, mianserin, maprotaline, trazodone, cyproheptadine, amitriptyline, doxepin, imipramine, nortriptyline, protriptyline, amoxapine, maprotiline, trazadone, fluoxetine and buprorion.

In the method of the invention, an effective amount of one or more antagonist of one class is mixed with an effective amount of one or more antagonist of a separate class. This combination of antagonists is then given to a patient with an excitable system disorder in conjunction, if desired, with a pharmaceutically acceptable carrier, diluent or excipient. Alternatively, in one embodiment of the invention each antagonist may be given separately to the patient at substantially the same time to provide for a combined therapy treatment.

Effective amounts of antagonists will vary depending on the potency of the drug and the nature of the disorder treated, as is known to those skilled in the art. However, general guidelines on dosages include up to about 0.25 mg/kg of each antagonist.

A further embodiment of the invention is a therapy using nicotinic, opioid, adrenergic and/or serotonergic antagonists in combination with agonists and/or non-steroidal anti-inflammatory drugs, stimulants, anti-depressants (e.g., antagonists of biogenic aminergic processes), and local anesthetics. The antagonists listed above are suitable for use in this embodiment of combined excitable system therapy.

Suitable opioid agonists and opioid peptides in this embodiment of the invention include (but are not limited to): morphine, fentanyl, sufentanil, codeine, meperidine, methadone, hydrocodone and hydromorphone.

Suitable nicotinic agonists include (but are not limited to): (−)-nicotine, (i)-methylpiperidine, (−)-cystisine, (−)-lobeline and (−)-anabasine.

Suitable non-steroidal anti-inflammatories include (but are not limited to): acetaminophen, aspirin, ibuprofen, naproxen, ketoprofen, flurbiprofen, sulindac, piroxicam, tolmetin, indomethacin, and ketorolac.

Suitable stimulants include (but are not limited to): methylphenidate, pemoline, cocaine, amphetamine, and ephedrine.

Suitable anti-depressants include (but are not limited to): methysergide, mianserin, maprotaline, trazodone, cyproheptadine, amitriptyline, doxepin, imipramine, nortriptyline, protriptyline, amoxapine, maprotiline, trazadone, fluoxetine and buprorion.

The compositions under the invention may be administered as a mixture of antagonists or agonists/antagonists, or may be independently and substantially simultaneously administered. In yet another embodiment, the individual antagonists and/or agonists can be administered at any time relative to one another so long as the combination of doses is therapeutically effective.

The route of administration of the composition of the invention may be oral, intravenous, nasal, rectal, or by any other pharmaceutically acceptable administration route, with intravenous and oral routes of administration being preferred.

The compositions of the invention may further include conventional additives such as stabilizers, buffers, such as phosphates, carbonates, citrates, and the like, salts, particularly sodium, potassium, calcium, magnesium, preservatives, such as EDTA, BHA, BHT, and the like, bulking agent and fillers, flavor enhancers, and the like as is known to one of ordinary skill in the art. The compositions may be in liquid, tablet, capsule, powder, or any other pharmaceutically acceptable form. Preferably, the composition of the invention (when mixed) or independently the antagonists and/or agonists are in the liquid, tablet or capsule forms. In one embodiment, the compositions are prepared in a timed-release form to provide for stabilized circulating levels of pharmaceutical agents. In another embodiment the compositions or, alternatively their components independently, are prepared in a liquid form in balanced saline and suitable for administration by injection. In yet another embodiment of the invention, the compositions may be administered by a trans-dermal patch or similar device.

EXAMPLE 1

An exemplary composition under the practice of the invention is the combination of the opioid antagonist naltrexone and the nicotinic antagonist mecamylamine. This combination has been shown to have anti-excitatory (anti-hyperalgesic) action and is likely to be useful in the treatment of hyperalgesic excitable system abnormalities, including (but not limited to) depression, pain, schizophrenia, and narcotic, tobacco and alcohol dependencies.

The opioid antagonist is preferred to be administered in a dosage of up to about 0.25 mg/kg. The nicotinic antagonist, for example, mecamylamine, is preferred in a dosage up to about 0.25 mg/kg.

The combination therapy may be administered in liquid form orally or, alternatively intravenously, once daily, twice daily or three times daily, in one embodiment of the invention. An acceptable liquid form includes use of about 0.9% buffered saline.

When treated with the inventive composition comprising naltrexone and mecamylamine under the present method, the patient exhibits stabilized excitable system activity with less excitatory influence.

EXAMPLE 2

A second exemplary composition of the invention is a combination of opioid antagonist naloxone and nicotinic antagonist mecamylamine. This combination is prepared in 0.9% buffered NaCl for oral administration every other day.

The opioid antagonist is administered in a dose up to about 0.25 mg/kg, depending on the characteristic excitable system activity and age of the particular patient. The dosage for mecamylamine is also up to about 0.25 mg/kg. When treated with the inventive composition and method, the patient exhibits stabilized (i.e., decreased) excitable system activity.

The foregoing disclosure is for the purposes of illustrating the invention and should not be construed as a limitation of the claims appended hereto. Moreover, in light of the disclosure herein, other embodiments of the invention will become obvious to those of ordinary skill in the art. The invention includes these modifications and alterations within its scope.

Each of the publications and patents cited herein is incorporated herein in their entireties by reference thereto.

I claim:

1. A composition for the treatment of excitable system abnormalities, pain and psychiatric disorders, comprising synergistic therapeutically effective amounts of mecamylamine and naltrexone in a pharmaceutically acceptable carrier.

2. The composition according to claim 1, wherein the mecamylamine and naltrexone are present in a dosage of up to about 0.25 mg/kg.

3. A method for treating excitable system abnormalities, pain and psychiatric disorders comprising:
   (a) providing a pharmacologically active composition comprising a pharmaceutical composition as set forth in claim 1; and
   (b) administering said pharmacologically active composition to a patient to provide for an increased or decreased excitable system activity in said patient.

4. The method according to claim 3, wherein said pharmacologic composition is administered orally, nasally, rectally, intravenously, epidurally or intrathecally.

5. The method according to claim 3, wherein said patient is a human.

6. The method according to claim 3, wherein said pharmacologically active composition comprises at least one opioid antagonist and at least one nicotinic antagonist.

7. The method according to claim 6, wherein said at least one opioid antagonist is naltrexone and wherein said at least one nicotinic antagonist is mecamylamine.

8. The method according to claim 7, wherein said therapeutically effective amounts are up to about 0.25 mg/kg mecamylamine and up to about 0.25 mg/kg naltrexone.

* * * * *